United States Patent [19]

Woo

[11] Patent Number: 4,493,799

[45] Date of Patent: Jan. 15, 1985

[54] SYNTHESIS OF SUCCINONITRILES

[75] Inventor: Edmund P. Woo, Midland, Mich.

[73] Assignee: The Dow Chemical Company, Midland, Mich.

[21] Appl. No.: 425,788

[22] Filed: Sep. 28, 1982

Related U.S. Application Data

[63] Continuation-in-part of Ser. No. 214,612, Dec. 9, 1980, abandoned.

[51] Int. Cl.$^3$ .................. C07C 121/28; C07C 121/60; C07C 120/02
[52] U.S. Cl. ........................... 260/465 H; 260/465 D; 260/465 E; 260/465 F; 260/465.4; 260/465.5 R; 260/465.6; 260/465.8 R
[58] Field of Search ......... 260/465 D, 465.4, 465.8 R, 260/465 H, 465 F, 465.6

[56] References Cited

U.S. PATENT DOCUMENTS 4,239,694 9/1979 Woo .............................. 260/465 D

OTHER PUBLICATIONS

Mowrey, D. T., J.A.C.S. 68, 2108 (1946).
Baker, W. et al., J. Chem. Soc., 127, 560 to 567, (1925).
Nagata, W. et al., Organic Reactions, vol. 25, W. G. Dauben Ed., Wiley 255-261, 358-367 (1977).

Primary Examiner—Joseph Paul Brust
Attorney, Agent, or Firm—Douglas N. Deline

[57] ABSTRACT

The process of hydrocyanating an α-cyanoacrylate ester with an alkali metal cyanide is improved by combining the reactants in an equivalent ratio of alkali metal cyanide to α-cyanoacrylate ester of from about 1:1 to about 1.1:1.

8 Claims, No Drawings

SYNTHESIS OF SUCCINONITRILES

CROSS-REFERENCE TO RELATED APPLICATION

This is a continuation-in-part of copending application Ser. No. 214,612, filed Dec. 9, 1980 now abandoned.

BACKGROUND OF THE INVENTION

The addition of cyanide to activated olefins is a well-known reaction. The preparation of polycyano compounds by the hydrocyanation and subsequent hydrolytic decarboxylation of α-cyanoacrylates was first proposed by D. T. Mowry, *J. Am. Chem. Soc.*, 68, 2108 (1946). He proposed a one-step process wherein the hydrocyanated ester intermediate was formed and then decarboxylated all in one reaction vessel without intermediate purification steps. The yield obtained (77 percent crude yield) was improved over the yields of earlier reported syntheses. The reference employed an 80 percent molar excess of cyanide.

SUMMARY OF THE INVENTION

It has now been discovered that employing an excess of cyanide reactant according to the above process is not needed in order to successfully produce the desired dicyano-substituted reaction product in high yields. To the contrary, not only does the use of excess cyanide produce undesirable environmental consequences due to the need to dispose of large quantities of cyanide-containing wastes, but it may even reduce the yield of desired dicyano-substituted reaction product compared to reactions employing equivalent amounts of reactants or at most a slight excess of cyanide.

This discovery is considered surprising in view of the general rule that more complete reaction of the limiting component of a reaction mixture is expected by use of an excess of one reactant.

Furthermore, a hither-to-before unreported serious hazard in the process proposed by Mowry is avoided according to the instant invention. It has been discovered during the course of the reaction that in addition to the expected by-products some of the cyano moieties present are inadvertently hydrolyzed to ammonium compounds. Most deleterious is the formation of ammonium cyanide which may sublime on the walls of the reaction vessel, condensing means, and other components of the reaction equipment. In the course of continuous large-scale production, this ammonium cyanide must be periodically removed to prevent plugging of the system and resulting superheating of the reaction mixture. The need to interrupt the reaction process for this necessary cleaning operation may be reduced considerably or even avoided by employing less cyanide reactant according to the instant invention.

DETAILED DESCRIPTION OF THE INVENTION

The process of the invention is most clearly illustrated by means of the following equations. The initial reactants are an alkali metal cyanide and an o-cyanoacrylate ester. The reaction is conducted in the presence of water or other source of hydroxide ions for the decarboxylation step. Preferred alkali metal cyanides are sodium cyanide and potassium cyanide. The process may be conducted as a single phase process or a biphasic process accompanied by the use of a phase-transfer catalyst.

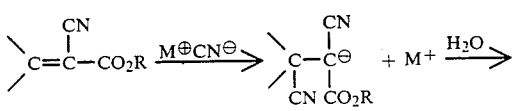

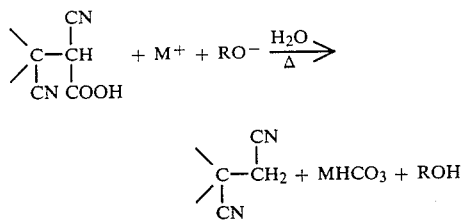

The instant invention comprises the above-described reaction of an alkali metal cyanide with α-cyanoacrylate esters wherein the ratio of cyanide reactant employed to α-cyanoacrylate ester in equivalents is from about 1:1 to about 1.1:1, and preferably from about 1:1 to about 1.05:1.

Practice of the instant invention has been found to greatly reduce the amount of undesirable by-products formed during the reaction while at the same time providing at least equivalent and often increased yields of succinonitrile product compared to use of a large excess of cyanide compound.

The α-cyanoacrylate ester for use according to the instant invention contains at least one reactive functional moiety of the formula:

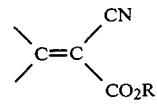

where R is a substituent of up to about 10 carbons selected from the group consisting of aryl, alkyl and aralkyl.

Examples of α-cyanoacrylate ester starting reactants include those having the formula

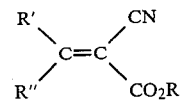

where R' and R'' independently each occurrence are hydrogens or substituents of up to about 10 carbons selected from the group consisting of aryl, alkyl, aralkyl and amino-, cyano-, nitro- hydroxy-, carboxy- and acetoxy-substituted derivatives thereof, and R is as previously defined.

Also included are difunctional α-cyanoacrylate esters. That is. compounds of the formula

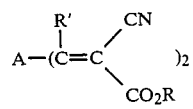

where A is $C_{1-6}$ alkylene, phenylene or

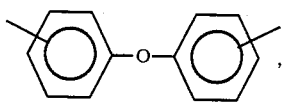

and R' and R are as previously defined.

Preferred α-cyano-substituted reactants are those wherein R is lower alkyl, R' is hydrogen or lower alkyl, R" is lower alkyl, phenyl or amino-, cyano-, hydroxy-, carboxy- or acetoxy-substituted derivatives thereof, and A is phenylene.

The α-cyanoacrylate ester and alkali metal cyanide reactants are combined in known manner in a solvent or solvent mixture able to dissolve sufficient amounts of both reactants. Peferred are solvent mixtures comprising water and one or more of the following: aliphatic and aromatic hydroxyl-substituted compounds having up to about 20 carbons including lower alkanols, glycols and alkyl and aryl monoethers of glycols; chlorinated hydrocarbons such as chloroform; aprotic polar solvents such as dimethylformamide, tetrahydrofuran, and dimethylsulfoxide, etc.; and combinations thereof. The components of the solvent mixture may be combined in any volume ratio. Suitably nearly equal volumes may be employed.

Under biphasic process conditions, suitable phase-transfer catalysts such as quaternary ammonium, phosphonium or sulfonium salts are employed. Preferred are quaternary ammonium halides such as benzyltriethyl ammonium chloride. The catalyst is employed in a small but effective amount, typically in a molar ratio from about 0.01 percent to about 5 percent based on alkali metal cyanide.

The reaction mixture is heated to elevated temperatures sufficient to allow the reaction to proceed and maintained at such temperature until the reaction is substantially complete. Suitable temperatures are generally from about 25° C. to about 200° C. and preferably from about 70° C. to about 110° C. Reaction times may be from about 2 hours to about 20 hours depending on the reaction temperature employed. In order to prevent degradation of the reaction product it is preferred to conduct the reaction in an unreactive atmosphere. For this purpose nitrogen or other inert gas may be employed.

Ordinary reaction vessels constructed of glass or metal may suitably be employed. Elevated or reduced pressures are not known to provide any process advantage but may be employed is so desired. Of course, elevated pressures necessarily result when employing temperatures above the boiling point of the solvent mixture.

The compounds formed, besides possessing utilities previously known in the art, are useful in the formation of diamines or of the corresponding dicarboxylic acids by known techniques. Such compounds are useful intermediates in the production of industrial chemicals. For example, the dicarboxylic acids are easily convertible to polyesters and other polymers or they may be converted to the corresponding anhydrides for use as plasticizers, industrial solvents or for further conversion to polymers or pharmaceutical compounds.

SPECIFIC EMBODIMENTS

Having described the invention, the following examples are provided to further illustrate the invented process and are not to be construed as limiting.

EXAMPLE 1

A reaction mixture comprising ethyl 2,6-dicyano-3-methyl-2-hexenoate (557 g, 2.7 moles) and NaCN (139 g, 2.84 moles) is combined with water (1.8 l) and ethanol (1.5 l, 95 percent) and stirred under a nitrogen atmosphere in a glass flask for 2¼ hours. The mixture is gradually heated to reflux temperature over an additional 2¼-hour period. The mixture is maintained at reflux temperature for an additional 4 hours.

Heating is thereupon discontinued and the reaction mixture filtered to remove sodium bicarbonate. The filtrate is evaporated until the volume of liquid is reduced to about ⅓ of the original volume and the product is then extracted with 3 500-ml portions of methylene chloride.

The methylene chloride volumes are combined and washed with saturated aqueous sodium chloride (1 liter) then dried over anhydrous MgSO$_4$. The solvent is then evaporated leaving a yellowish viscous liquid; yield 418 g, 96 percent.

Distillation of a portion of the product gives an identical product having a boiling point no different from the undistilled product.

EXAMPLE 2

The reaction conditions of Example 1 are repeated except that a 50 percent mole excess of NaCN is employed. Accordingly, ethyl 2,6-dicyano-3-methyl-2-hexenoate (447 g, 2.17 moles) and NaCN (159 g, 3.255 moles) are combined in a solution of water (1.5 l) and ethanol (1.4 l) and refluxed for 5 hours. After working up, a dark brown oil remains which has to be distilled to purify. The distillation is conducted at 0.5 Torr and the fraction obtained at 170° C.–180° C. is identified as the desired 1,2,5-tricyano-2-methylpentane by infrared spectrum. Yield is 53.6 percent. Not only is a purification step required to obtain the desired product but a significant reduction in yield results from the use of excess cyanide reactant.

EXAMPLE 3

In the following reactions the reactive α-cyanoacrylate ester employed is diethyl 3,3'-(1,4-phenylene)bis(2-cyano-2-propenoate) containing 2 reactive acrylate moieties per molecule. In one run the solvent employed comprises equal volumes of isopropanol and water consequently resulting in a higher reflux temperature compared to runs employing equal volumes of ethanol and water. In all cases the isolated product obtained is 1,4-di(1,2-dicyanoethyl)benzene. Results are contained in Table I.

TABLE I

| Run | Alcohol | Acrylate (moles) | NaCN (moles) | Equivalent Ratio NaCN/Acrylate | Yield (%) |
| --- | --- | --- | --- | --- | --- |
| 1 | isopropanol | 1.0 | 2.0 | 1.0:1.0 | 82.4 |
| 2 | ethanol | 0.1 | 0.21 | 1.05:1.0 | 90.5 |
| 3 | ethanol | 1.0 | 2.1 | 1.05:1.0 | 82.4 |
| 4 | ethanol | 0.1 | 0.24 | 1.2:1.0 | 60.0 |

It is seen that use of a 20 mole percent excess of sodium cyanide in Run 4 leads to a significant decrease in product yield which is unexplained by other reaction conditions.

EXAMPLE 4

A mixture of-ethyl 2-cyano-3-(4-hydroxyphenyl)-2-propenoate (150 g, 0.69 mole), sodium cyanide (35.8 g, 0.73 mole, 5.8 percent excess), chloroform (500 ml), water (450 ml) and benzyltriethylammonium chloride (3.5 g), is stirred under nitrogen at room temperature for 50 minutes. By this time, all the solid reagents are dissolved. Concentrated hydrochloric acid (115 ml) is added to the mixture and the chloroform layer removed. The residue is extracted with ethyl acetate. Each of the organic layers is washed with water and dried over anhydrous magnesium sulfate. Upon removal of the solvents, 22.4 g (13.4 percent) of ethyl 2,3-dicyano-3-(4-hydroxyphenyl)propionate is isolated from the chloroform layer, and 140 g (83 percent) of the same product is isolated from the ethyl acetate layer. The combined yield is 96.4 percent.

What is claimed is:

1. A process for preparing a succinonitrile corresponding to the formula:

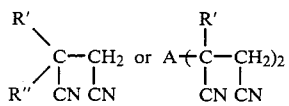

wherein:
   $R'$ and $R''$ are independently each occurrence hydrogen or a substituent of up to about 10 carbons selected from the group consisting of aryl, alkyl, aralkyl and amino-, cyano-, nitro-, hydroxy-, carboxy-and acetoxy-substituted derivatives thereof; and
   A is $C_{1-6}$ alkylene, phenylene or

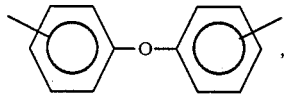

comprising contacting an α-cyanoacrylate ester corresponding to the formula:

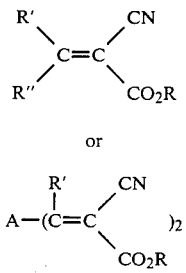

wherein
   $R'$, $R''$ and A are as previously defined, and
   R is a substituent of up to about 10 carbons selected from the group consisting of aryl, alkyl and aralkyl,
with an alkali metal cyanide in a ratio of from about 1 to about 1.1 equivalents of cyanide reactant for each equivalent of α-cyanoacrylate ester reactant in a solvent mixture comprising water and a member selected from the group consisting of aliphatic and aromatic hydroxyl-containing compounds having up to about 20 carbons, chlorinated hydrocarbons and aprotic polar solvents at an elevated temperature.

2. A process according to claim 1 wherein from about 1 to about 1.05 equivalents of cyanide reactant are contacted with each equivalent of α-cyanoacrylate ester reactant.

3. A process according to claim 1 wherein the temperature is from about 25° C. to about 200° C.

4. A process according to claim 3 wherein the temperature is from about 70° C. to about 110° C.

5. A process according to claim 1 wherein the alkali metal cyanide is sodium cyanide or potassium cyanide.

6. A process according to claim 1 wherein R is lower alkyl, $R'$ is hydrogen or lower alkyl, $R''$ is lower alkyl, phenyl or amino-, cyano-, nitro-, hydroxy-, carboxy- or acetoxy-substituted derivatives thereof, and A is phenylene.

7. A process according to claim 6 wherein the α-cyanoacrylate ester is ethyl 2,6-dicyano-3-methyl-2-hexenoate or diethyl 3,3'-(1,4-phenylene)bis(2-cyano-2-propenoate).

8. A process according to claim 1 which is a biphasic process and a phase-transfer catalyst is additionally present.

* * * * *

UNITED STATES PATENT AND TRADEMARK OFFICE
CERTIFICATE OF CORRECTION

PATENT NO. : 4,493,799
DATED : January 15, 1985
INVENTOR(S) : Edmund P. Woo

It is certified that error appears in the above-identified patent and that said Letters Patent is hereby corrected as shown below:

Column 1, line 64, "o-cyanoacrylate" should read -- α-cyano-acrylate --.

Column 2, line 61, "That is. compounds" should read -- That is, compounds --.

Column 3, line 17, "Peferred" should read -- Preferred --.

Column 3, line 54, "is so desired" should read -- if so desired --.

Column 5, line 8, "of-ethyl" should read -- of ethyl --.

Signed and Sealed this

Ninth Day of July 1985

[SEAL]

Attest:

DONALD J. QUIGG

Attesting Officer     Acting Commissioner of Patents and Trademarks